United States Patent [19]

Frickel et al.

[11] 4,305,951
[45] Dec. 15, 1981

[54] NOVEL AMINO DERIVATIVES OF 5-(2-HYDROXYSTYRYL)-ISOXAZOLE, THEIR PREPARATION AND THERAPEUTIC FORMULATIONS CONTAINING THESE COMPOUNDS

[75] Inventors: Fritz-Frieder Frickel, Deidesheim; Peter C. Thieme; Albrecht Franke, both of Wachenheim; Hans Theobald, Limburgerhof; Dieter Lenke, Ludwigshafen; Josef Gries, Wachenheim, all of Fed. Rep. of Germany

[73] Assignee: BASF Aktiengesellschaft, Fed. Rep. of Germany

[21] Appl. No.: 199,835

[22] Filed: Oct. 23, 1980

[30] Foreign Application Priority Data

Oct. 26, 1979 [DE] Fed. Rep. of Germany ....... 2943405

[51] Int. Cl.$^3$ ............................................ C07D 261/08
[52] U.S. Cl. .................................... 424/272; 542/429; 542/430; 542/455

[58] Field of Search ................ 424/272; 542/455, 429, 542/430

[56] References Cited

U.S. PATENT DOCUMENTS 3,624,079 11/1971 Lednicer ............................. 542/455
4,251,539 2/1981 Thieme et al. ...................... 542/455

FOREIGN PATENT DOCUMENTS 2007751 9/1970 Fed. Rep. of Germany .
1939809 2/1971 Fed. Rep. of Germany .
2624918 12/1977 Fed. Rep. of Germany .
451115 5/1968 Switzerland .
1307436 2/1973 United Kingdom .

Primary Examiner—Arthur P. Demers
Attorney, Agent, or Firm—Keil & Witherspoon

[57] ABSTRACT

Novel aminopropanol derivatives of 5-(2-hydroxystyryl)-isoxazole and their addition salts with acids, their preparation, pharmaceutical formulations containing these compounds, and their use in the treatment of hypertonia, coronary heart disease and cardiac arrhythmias.

4 Claims, No Drawings

NOVEL AMINO DERIVATIVES OF 5-(2-HYDROXYSTYRYL)-ISOXAZOLE, THEIR PREPARATION AND THERAPEUTIC FORMULATIONS CONTAINING THESE COMPOUNDS

The present invention relates to novel aminopropanol derivatives of 5-(2-hydroxystyryl)-isoxazole and their addition salts with acids, their preparation, pharmaceutical formulations containing these compounds, and their use in the treatment of hypertonia, coronary heart disease and cardiac arrhythmias.

We have found that compounds of the general formula I

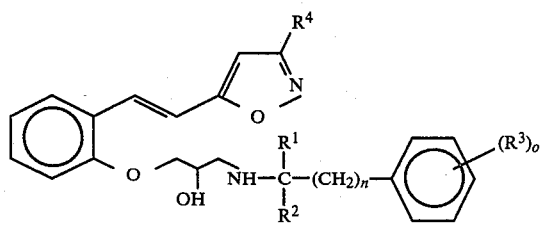

where n is 1 or 2, o is 1, 2 or 3, $R^1$ and $R^2$ are each hydrogen or straight-chain or branched alkyl of 1 to 5 carbon atoms, $R^3$ is hydrogen, hydroxyl, halogen, alkyl, alkoxy or alkylthio of 1 to 5 carbon atoms (the last-mentioned three groups each being unsubstituted, or mono-, di- or tri-substituted by halogen or monosubstituted by hydroxyl or alkoxy of 1 to 3 carbon atoms), alkenyl, alkynyl, alkynyloxy or cycloalkoxy, each of 2 to 6 carbon atoms in the alkyl and of 3 to 8 carbon atoms in the ring, or amino which is unsubstituted or is mono- or di-substituted by alkyl of 1 to 5 carbon atoms, and if o is 2 or 3, the $R^3$'s may be identical or different, or $R^3$ is methylenedioxy or alkylene of 3 or 4 carbon atoms, and $R^4$ is alkyl of 1 to 4 carbon atoms, and their addition salts with acids, possess valuable pharmacological properties.

For $R^3$, examples of halogen are fluorine and chlorine, examples of unsubstituted and substituted alkyl, alkoxy and alkylthio are methyl, ethyl, propyl, n-butyl, tert.-butyl, methoxy, ethoxy, propoxy, trifluoromethyl, hydroxymethyl, 1-hydroxyethyl, methoxymethyl, ethoxymethyl, 1-methoxyethyl and n-propoxymethyl, examples of unsaturated radicals are vinyl, allyl and propargyloxy, examples of cycloalkoxy are cyclopentoxy and cyclohexoxy and an example of amino is di-methylamino.

If $R^3$ is trimethylene or tetramethylene, the compound is an indanyl or tetrahydronaphthyl derivative, containing, for example, the 4-indanyl, 5-indanyl, 5,6,7,8-tetrahydro-1-naphthyl or 5,6,7,8-tetrahydro-2-naphthyl system.

Amongst the meanings mentioned, the preferred meanings of $R^1$ and $R^2$ are hydrogen and methyl, the preferred meanings of $R^3$ are hydrogen, chlorine, trifluoromethyl, alkyl of 1 to 4 carbon atoms, methoxy, hydroxyl and dimethylamino, the $R^3$'s, if two or three are present, being identical or different, as well as methylenedioxy, and the preferred meanings of $R^4$ are methyl and ethyl.

Accordingly, examples of compounds according to the invention are: 3-methyl-5-[2-[2-hydroxy-3-(2-(3-trifluoromethylphenyl)-1,1-dimethylethylamino)-propoxy]-styryl]-isoxazole, 3-ethyl-5-[2-[2-hydroxy-3-(3-(4-hydroxyphenyl)-1-methylpropylamino)-propoxy]-styryl]-isoxazole, 3-methyl-5-[2-[2-hydroxy-3-(3-(4-hydroxyphenyl)-1-methylpropylamino)-propoxy]-styryl]-isoxazole, 3-methyl-5-[2-[2-hydroxy-3-(2-(3,4-dimethoxyphenyl)-1-ethylamino)-propoxy]-styryl]-isoxazole, 3-methyl-5-[2-[2-hydroxy-3-(3-phenyl-1-methylpropylamino)-propoxy]styryl]-isoxazole, 3-methyl-5-[2-[2-hydroxy-3-(2-(4-methoxyphenyl)-1-ethylamino)-propoxy]-styryl]-isoxazole, 3-methyl-5-[2-[2-hydroxy-3-(2-(3,4-dimethoxyphenyl)-1-methylethylamino)-propoxy]-styryl]-isoxazole, 3-methyl-5-[2-[2-hydroxy-3-(2-(4-methoxyphenyl)-1-methylethylamino)-propoxy]-styryl]-isoxazole, 3-methyl-5-[2-[2-hydroxy-3-(2-(2-methoxyphenyl)-1-methylethylamino)-propoxy]-styryl]-isoxazole, 3-methyl-5-[2-[2-hydroxy-3-(2-(2-methoxyphenyl)-1,1-dimethylethylamino)-propoxy]-styryl]-isoxazole, 3-methyl-5-[2-[2-hydroxy-3-(2-(4-methoxyphenyl)-1,1-dimethylethylamino)-propoxy]-styryl]-isoxazole, 3-methyl-5-[2-[2-hydroxy-3-(3-(4-dimethylaminophenyl)-1-methylpropylamino)-propoxy]-styryl]-isoxazole, 3-methyl-5-[2-[2-hydroxy-3-(3-(4-hydroxyphenyl)-1,1-dimethylpropylamino)-propoxy]-styryl]-isoxazole, 3-methyl-5-[2-[2-hydroxy-3-(2-phenyl-1,1-dimethylethylamino)-propoxy]-styryl]-isoxazole, 3-methyl-5-[2-[2-hydroxy-3-(3-(3,4-methylenedioxyphenyl)-1-methylpropylamino)-propoxy]-styryl]-isoxazole, 3-methyl-5-[2-[2-hydroxy-3-(3-(4-methoxyphenyl)-1,1-dimethylpropylamino)-propoxy]-styryl]-isoxazole, 3-methyl-5-[2-[2-hydroxy-3-(3-(3,4-dimethoxyphenyl)-1-methylpropylamino)-propoxy]-styryl]-isoxazole, 3-methyl-5-[2-[2-hydroxy-3-(2-(3-trifluoromethylphenyl)-1-methylethylamino)-propoxy]-styryl]-isoxazole, 3-methyl-5-[2-[2-hydroxy-3-(2-(4-chlorophenyl)-1,1-dimethylethylamino)-propoxy]-styryl]-isoxazole, 3-methyl-5-[2-[2-hydroxy-3-(3-(3,4,5-trimethoxyphenyl)-1-methylpropylamino)-propoxy]-styryl]-isoxazole and 3-methyl-5-[2-[2-hydroxy-3-(2-(4-hydroxyphenyl)-1,1-dimethylethylamino)-propoxy]-styryl]-isoxazole.

Further examples of compounds according to the invention are: 3-methyl-5-[2-[2-hydroxy-3-(2-(4-hydroxyphenyl)-1-methylethylamino)-propoxy]-styryl]-isoxazole and 3-methyl-5-[2-[2-hydroxy-3-(2-(2-hydroxyphenyl)-1,1-dimethylethylamino)-propoxy]-styryl]-isoxazole.

To prepare compounds according to the invention, a 3-alkyl-5-styryl-isoxazole of the general formula (II)

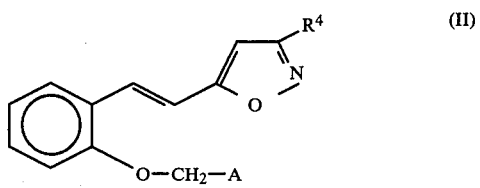

where $R^4$ has the meanings given for formula I and A is

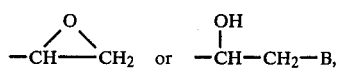

B being a nucleofugic leaving group, is reacted with an amine of the general formula (III)

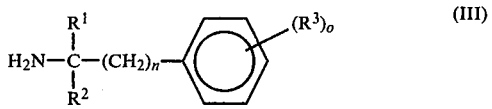

where $R^1$, $R^2$, $R^3$, n and o have the meanings given for formula I, in a conventional manner, advantageously in a solvent and in the presence or absence of an acid acceptor, after which the compound obtained is converted, if required, into an addition salt with a physiologically tolerated acid.

The leaving group B is preferably halogen, especially chlorine, bromine or iodine. Further examples of suitable nucleofugic leaving groups are aromatic and aliphatic sulfonic acid radicals, eg. the p-toluenesulfonic acid, p-bromobenzenesulfonic acid or methanesulfonic acid radical.

The reaction is carried out at from 10° to 120° C., ie. at room temperature or above, advantageously at from 50° to 120° C., under atmospheric pressure or in a closed vessel under superatmospheric pressure, with or without heating at a temperature within the stated range.

The starting compounds may be reacted direct, ie. without addition of a diluent or solvent. Advantageously, however, the reaction is carried out in the presence of a lower alcohol of 1 to 4 carbon atoms, eg. methanol, ethanol or a propanol, isopropanol and ethanol being preferred, a lower saturated dialkyl ether, dialkyl glycol ether or cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, dimethyl sulfoxide or water, or a mixture of the said solvents.

Preferred solvents for the reaction of 3-methyl-5-[2-(2,3-epoxypropoxy)-styryl]-isoxazole with one of the above amines (III) are lower alcohols, especially ethanol and isopropanol, the reaction preferably being carried out at from 50° C. to 120° C. under atmospheric pressure. In the case of the nucleophilic replacement of a radical B, preferred solvents are lower aliphatic ketones, eg. acetone and methyl isobutyl ketone, cyclic ethers, especially tetrahydrofuran and dioxane, and dialkylformamides, eg. dimethylformamide, and the reaction is preferably carried out at from 90° to 120° C. A catalytic amount of sodium iodide or potassium iodide may or may not be employed in the reaction.

A mixture of an epoxide and a halohydrin may also be employed as the starting compound of the formula II, since such mixtures are under certain circumstances formed in the industrial manufacture of a compound of the formula II.

In an advantageous embodiment of the nucleophilic replacement of the radical B by the amine used, the reaction is carried out in the presence of a base as an acid acceptor. Preferred bases are alkali metal hydroxides, carbonates, bicarbonates and alcoholates, and tertiary organic amines, such as pyridine or a trialkylamine, eg. trimethylamine or triethylamine. Amongst the alkali metal compounds, those of sodium or potassium are particularly suitable. The base is employed in stoichiometric amount or in slight excess. It can be advantageous to use an excess of the amine III employed for the reaction, so that it also serves as the acid acceptor.

The time required to complete the reaction depends on the reaction temperature and is in general from 2 to 15 hours. The product can be isolated in a conventional manner, for example by filtration or by distillation of the diluent or solvent from the reaction mixture. Purification of the compound obtained is effected in a conventional manner, for example by recrystallization from a solvent, conversion to an addition salt with an acid, or column chromatography.

A starting compound of the formula (II) may be obtained by alkylating a 3-alkyl-5-(2-hydroxy-styryl)isoxazole (which is prepared, for example, in a Wittig reaction from a dialkyl-isoxazolyl-5-methylene-phosphonate and a salicylaldehyde, carrying a protective group on the OH, in accordance with German Patent Application P 28 18 998.2) with an epihalohydrin or an α,ω-dihalopropan-2-ol. Suitable epihalohydrins are epichlorohydrin, epibromohydrin and epiiodohydrin, and suitable α,ω-dihalo-propan-2-ols are, in particular, 1,3-dichloro-propan-2-ol and 1,3-dibromo-propan-2-ol.

The reaction of the 3-alkyl-5-(2-hydroxystyryl)-isoxazole, to prepare a starting compound of the formula III, is advantageously carried out at from 0° to 120° C. under atmospheric pressure or in a closed vessel under superatmospheric pressure. Advantageously, the preparation is carried out in an inert diluent or solvent, for example a lower aliphatic ketone, eg. acetone, methyl ethyl ketone or methyl isobutyl ketone, a lower alcohol of 1 to 4 carbon atoms, eg. methanol, ethanol, propanol or butanol, a lower aliphatic or cyclic ether, eg. diethyl ether, tetrahydrofuran or dioxane, a dialkylformamide, eg. dimethylformamide, diethylformamide, dimethylsulfoxide or hexamethylphosphorotriamide, or with excess alkylating agent as the diluent or solvent.

The reactions are preferably carried out in the presence of a base as the acid acceptor. Suitable bases are alkali metal carbonates, bicarbonates, hydroxides, hydrides and alcoholates, especially those of sodium and potassium, basic oxides, eg. aluminum oxide and calcium oxide, and organic tertiary bases, such as pyridine, piperidine and lower trialkylamines, eg. trimethylamine and triethylamine. In relation to the alkylating agent employed, the bases may be present in catalytic amount or stoichiometric amount or even in slight excess.

Preferably, a 3-alkyl-5-(2-hydroxy-styryl)isoxazole is reacted with epibromohydrin or 1,2-dibromopropan-2-ol in a polar aprotic solvent, especially dimethylsulfoxide, in the presence of not less than one mole equivalent of base, especially of sodium hydride, per mole of alkylating agent, at from 0° to 50° C.

Similarly to the process for the reaction of phenol with 1,3-dichloro-propan-2-ol described in Liebigs Annalen der Chemie (1976), 221–224, a 3-alkyl-5-(2-hydroxy-styryl)-isoxazole may also be reacted with the equivalent amount of 1,3-dichloro-propan-2-ol in aqueous sodium hydroxide solution at about 50° C.

The starting compounds of the general formula II, in which A is

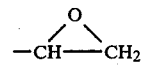

may also be obtained by reacting a methanephosphonic acid ester of the general formula IV

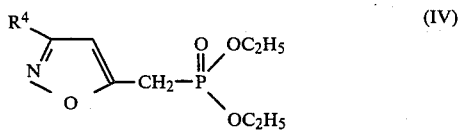

with o-(2,3-epoxypropoxy)-benzaldehyde, described in J. Chem.Soc. London (1974), 1,571–1,577.

Suitable reaction media for the reaction of o-(2,3-epoxypropoxy)-benzaldehyde with a phosphorane of the formula IV are inert organic solvents, for example a lower saturated dialkyl ether, dialkyl glycol ether or cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, dimethylsulfoxide, dimethylformamide and mixtures of the said solvents. The reactions are carried out at from 0° C. to the boiling point of the solvent used, advantageously at room temperature, for from 1 to 48 hours, preferably from 1 to 16 hours, and advantageously in a nitrogen atmosphere. Suitable bases for this Wittig-Horner reaction are alkali metal hydrides, amides and alcoholates, especially those of sodium and potassium, sodium methylate being preferred.

In a further method of preparation of the novel compounds, a methanephosphonic acid ester of the formula IV is reacted with a compound of the formula V in the presence of a base and advantageously in the presence of a solvent, in a conventional manner, under the conditions of a Wittig-Horner reaction

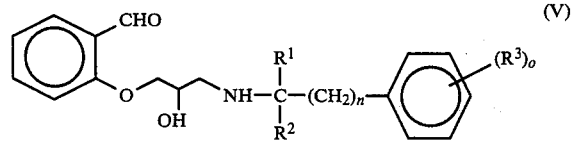

These reactions may be carried out, for example, under the conditions described in German Laid-Open Application DOS No. 1,939,809.

The Wittig-Horner reaction is advantageously carried out in an inert diluent or solvent, for example a lower saturated dialkyl ether, dialkyl glycol ether or cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, dimethylsulfoxide or a mixture of the said solvents. Advantageously, the reaction is carried out at ambient temperature or by heating at 30°–80° C. Suitable bases are alkali metal hydrides, amides and alcoholates, especially those of sodium and of potassium, and butyl-lithium and phenyl-lithium.

Because of their carbon-carbon double bond, the novel compounds can be in the form of mixtures of the cis- and trans-isomers, which can be separated by conventional physico-chemical methods, for example by fractional crystallization, chromatography or sublimation.

The novel compounds of the formula (I) possess a chirality center on carbon atom 2 of the aliphatic aminopropanol side chain and are obtained as racemates which can be separated into the optically active antipodes by conventional methods, for example by formation of diastereomeric salts with optically active auxiliary acids, such as dibenzoyltartaric acid, camphor-10-sulfonic acid, ditoluyltartaric acid or 3-bromocamphor-8-sulfonic acid and separation of these salts by crystallization.

Depending on the choice of the particular amine (III), some of the novel compounds of the formula (I) may have a second asymmetric carbon atom and can then be in the form of diastereomer mixtures which can be separated into diastereomer pairs by physico-chemical methods, in a conventional manner. Optically pure forms of the novel compounds possessing two chirality centers can be obtained if an optically active amine of the general formula (III) is employed and the two diastereomers are subsequently separated, for example by fractional crystallization or chromatography.

If required, a novel compound obtained is converted to an addition salt with a physiologically tolerated acid. Examples of conventional suitable physiologically tolerated acids are, amongst inorganic acids, hydrochloric acid, hydrobromic acid, phosphoric acid and sulfuric acid, and, amongst organic acids, maleic acid, fumaric acid, lactic acid, tartaric acid, malic acid, citric acid, salicylic acid, adipic acid and benzoic acid; others may be found in Fortschritte der Arzneimittelforschung, published by Birkhäuser, Basel and Stuttgart, 10 (1966), 224–225, and J. Pharmac. Sci., 66 (1977), 1–5.

The addition salts with acids are as a rule obtained in a conventional manner by mixing the free base or a solution thereof with the appropriate acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. To cause better crystallization, mixtures of the above solvents may also be used. Furthermore, pharmaceutically useful aqueous solutions of addition salts of the aminopropanol derivatives of the general formula (I) with acids may be prepared by dissolving a free base of the general formula (I) in an aqueous acid solution.

The novel compounds, and their physiologically tolerated addition salts with acids, exhibit valuable pharmacological properties.

Pharmacodynamically, they act as $\beta$-sympatholytic agents which produce an acute hypotensive effect. This type of effect differs from that of the conventional $\beta$-sympatholytic agents, for example propranolol. The latter does not have a hypotensive effect in acute test conditions. Because of the said effect, the compounds are particularly suitable for the pharmacotherapeutic treatment of hypertonia, coronary heart disease (angina pectoris) and cardiac arrhythmias.

The pharmacodynamic properties were investigated by the following methods:

1. $\beta$-Sympatholytic action

Isoproterenol (0.1 $\mu$g/kg administered intravenously) produces increases averaging 121±2.1 min$^{-1}$ in the pulse rate of pithed rats (Sprague-Dawley, ♂, weight 200–240 g), the initial pulse rate being about 268±3.9 min$^{-1}$ (N=100).

$\beta$-Sympatholytic agents have a specific and dose-dependent inhibiting action on this increase in pulse rate. The substances tested are administered 5 minutes before the isoproterenol. The ED 50% is determined as the dose which inhibits the isoproterenol-induced tachycardia by 50%.

2. Hypotensive action on narcotized rats

To test the hypotensive action, the compounds are administered intravenously to male Sprague-Dawley rats (weight: 230-280 g) under urethane narcosis (1.78 g/kg administered intraperitineally).

The blood pressure in the carotid artery is measured by means of a Statham transducer. The ED 20% is determined as the dose which lowers the mean carotid pressure by 20%.

3. Acute toxicity in mice

To determine the acute toxicity (LD 50), the compounds are administered intraperitoneally to female NMRI mice (weight: 22-26 g).

The effective doses (see 1. and 2.) are calculated from the linear relationships between the logarithm of the dose and the logarithm of the action, by means of regression analysis. The LD 50 (see 3.) was determined by means of Probit analysis. The reference substance used was the known β-sympatholytic agent propranolol.

The β-sympatholytic activity (see the Table) of the compounds of Examples 3 and 4 corresponds approximately to that of propranolol.

In addition to the β-sympatholytic action, the novel compounds possess—in contrast to propranolol—an acute hypotensive action, which is dose-dependent. Intravenous injection of 0.49 mg/kg of the compound of Example 3 or 0.7 mg/kg of the compound of Example 4 into rats triggers a 20% lowering of the blood pressure. In contrast, propranolol, up to doses of 2.15 mg/kg, does not lower the blood pressure. It is only the sub-lethal dose of 4.64 mg/kg which lowers the blood pressure, by an average of 36%.

In addition to the pharmacotherapeutically important effects of lowering the blood pressure and of β-sympatholysis, the compounds mentioned have a low toxicity. The lethal dose for the compound of Example 3 is 24,600 times as great, and for the compound of Example 4, 29,900 times as great, as the β-sympatholytically effective dose. For propranolol, the lethal dose is only 8,500 times greater than the effective dose.

| Example number | β-Sympatholytic action[1] | | Hypotensive action[2] | Lethal action[4] | |
|---|---|---|---|---|---|
| | ED 50% | R.A. | ED 20% | LD 50 | Q[5] |
| 3 | 0.0106 | 1.20 | 0.49 | 261 | 24,600 |
| 4 | 0.0215 | 0.59 | 0.70 | 642 | 29,900 |
| Propranolol | 0.0127 | 1.00 | [3] | 108 | 8,500 |

[1] Pithed rats. Intravenous administration. ED 50% = dose [in mg/kg] which inhibits the isoproterenol-induced increase in pulse rate by 50%. R.A. = relative activity. Propranolol = 1.00.
[2] Rats. Urethane narcosis. Intravenous administration. ED 20% = dose [in mg/kg] which lowers the blood pressure by 20%.
[3] At 2.15 mg/kg the blood pressure is increased by 11%; at 4.64 mg/kg it is lowered by 36%; at 10 mg/kg 2 out of 6 animals died.
[4] Mice. Intraperitoneal administration. LD 50 in mg/kg
[5] $Q = \frac{LD\ 50}{ED\ 50\%}$ Accordingly, the present invention also relates to therapeutic agents or formulations which contain a compound of the formula (I) or a physiologically tolerated acid addition salt thereof, as the active compound, together with conventional carriers and diluents, and to the use of the novel compounds for therapeutic purposes.

The therapeutic agents or formulations are prepared in a conventional manner by compounding an appropriate dose with the conventional liquid or solid carriers or diluents and the conventional pharmaceutical auxiliaries, in accordance with the desired route of administration.

The preferred formulations are those suitable for oral administration. Examples of these are tablets, film tablets, dragees, capsules, pills, powders, solutions, suspensions or forms which have a depot effect.

Parenteral formulations, such as injection solutions, may of course also be used. Further examples of suitable formulations include suppositories.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets may also consist of a plurality of layers.

Accordingly, dragees may be prepared by coating cores, prepared in a similar manner to the tablets, with agents conventionally used in dragee coatings, for example polyvinylpyrrolidone or shellac, gum arabic, talc, titanium dioxide or sugar. The dragee shell can also consist of several layers, in which the auxiliaries, mentioned above in connection with tablets, may be used.

Solutions or suspensions containing the novel active compounds may additionally contain sweeteners, eg. saccharin, cyclamate or sugar, and, for example, flavorings, such as vanillin or orange extract. They may furthermore contain suspending agents, such as sodium carboxymethylcellulose, or preservatives, such as p-hydroxybenzoates. Capsules containing the active compounds may be prepared, for example, by mixing the latter with an inert carrier, such as lactose or sorbitol, and encapsulating the mixture in gelatin capsules.

Suitable suppositories may be prepared, for example, by mixing the active compound with an appropriate carrier for this purpose, such as a neutral fat or polyethylene glycol or derivative thereof.

Individual doses of the novel compounds suitable for man are from 1 to 100 mg, preferably from 3 to 50 mg.

The Examples which follow illustrate the present invention.

PREPARATION OF INTERMEDIATES

Compound I: o-(α-Methoxy-ethoxy)-benzaldehyde (a) 610 g (5 moles) of salicylaldehyde are dissolved in 1.5 liters of xylene; 900 g (5 moles) of a 30% strength NaOCH₃ solution in methanol are added dropwise thereto, at 40°-50° C. The mixture is then heated and the mthanol is distilled off and progressively replaced, in the reaction flask, by an equal amount of xylene. Heating is continued until the xylene begins to distil (passing over at about 130° C.). The suspension of the Na salt of salicylaldehyde is then cooled to 60° C. and reacted further as described under (c).

(b) 200 ml of xylene are mixed with a pinch of hydroquinone, the mixture is cooled to from −20° to −30° C., and 290 g (5 moles) of vinyl methyl ether are condensed therein. 183 g (5 moles) of HCl gas are then introduced at −30° C. and the solution is left to stand, so that it reverts to room temperature. The resulting 1-chloroethyl methyl ether solution is reacted further as described under (c).

(c) The solution of 1-chloroethyl methyl ether, prepared as described under (b), is added dropwise to the solution, at 60° C., of the Na salt of salicylaldehyde (see a), and the batch is stirred for about 1½ hours at 60° C.; the pH is then brought to 8–9, if necessary, by means of 30% strength NaOCH₃ solution, and stirring is continued overnight, at room temperature.

The sodium chloride which has precipitated is then filtered off and washed with xylene, and the xylene is distilled from the combined filtrates on a rotary evaporator. The resulting residue is distilled through a column, under 2 mm Hg. 690 g of o-(α-methoxy-ethoxy)-benzaldehyde, boiling point 94°–96° C./2 mm Hg, are obtained.

Compound II: Diethyl (3-methylisoxazol-5-yl)-methanephosphonate 445 g of 5-chloromethyl-3-methylisoxazole and 674 g of triethyl phosphite are slowly heated to 150° C. and kept at this temperature for 4 hours. After distillation, 546 g (69% of theory) of diethyl (3-methylisoxazol-5-yl)-methanephosphonate, of boiling point 118°–121° C./0.3 mm Hg, are obtained.

$^1$H-NMR spectrum (CHCl₃, with TMS as internal standard): $\tau = 3.85$ (d, J=3 Hz, 1H), 4.17 (m, J=8 Hz, 4H), 6.67 (d, J=22 Hz, 2H), 7.72 (s, 3H) and 8.67 (t, J=8 Hz, 6H).

$C_9H_{16}NO_4P$ (233.21): calculated: C 46.35%; H 6.91%; N 6.01%; P 13.28%. found: C 45.9%; H 7.0%; N 6.0%; P 13.0%.

Compound III: Diethyl (3-ethylisoxazol-5-yl)-methanephosphonate 15 g of 5-chloromethyl-3-ethyl-isoxazole and 18 g of triethyl phosphite are slowly heated to 150° C. and kept at this temperature for 2½ hours. After cooling, the residue is distilled under reduced pressure. 18.2 g of diethyl (3-ethylisoxazol-5-yl)-methanephosphonate, of boiling point 120°–121° C./0.2 mm Hg are obtained. Yield: 71.2%.

$^1$H-NMR spectrum (CDCl₃, with TMS as internal standard): $\tau = 3.85$ (d, J=3 Hz, 1H), 4.17 (m, J=Hz, 4H), 6.60 (d, H=20 Hz, 2H), 7.35 (q, J=Hz, 2H) and 8.50–8.93 (m, 9H).

$C_{10}H_{18}NO_4P$ (247.23): calculated: C 48.58%; H 7.34%; N 5.67%; P 12.53%. found: C 48.4%; H 7.1%; N 5.7%; P 12.3%.

The two phosphonate esters shown below are prepared similarly.

Diethyl (3-isopropyl-isoxazol-5-yl)-methanephosphonate: boiling point 117°–122° C./0.3 mm Hg; yield 73%.

Diethyl (3-tert.-butyl-isoxazol-5-yl)-methanephosphonate: boiling point 126°–132° C./0.3 mm Hg: yield 88%.

PREPARATION OF STARTING COMPOUNDS

EXAMPLE I

3-Methyl-5-(2-hydroxy-styryl)-isoxazole 8.8 g (0.2 mole) of a 55% strength suspension of sodium hydride in paraffin oil are introduced into 100 ml of absolute dimethylsulfoxide. 47 g (0.2 mole) of diethyl (3-methyl-isoxazol-5-yl)-methanephosphonate are added dropwise at room temperature. The mixture is then stirred for 30 minutes, after which 36 g (0.2 mole) of o-(1-methoxyethoxy)-benzaldehyde are added dropwise, with continued stirring. The reaction mixture is then stirred for 24 hours at room temperature and is poured onto 1 liter of ice water, and the batch is extracted 3 times with 80 ml of methylene chloride at a time. The combined organic phases are dried with sodium sulfate and evaporated down on a rotary evaporator. The oily residue is dissolved in 80 ml of methanol and 10 ml of water, 2 ml of 5 N HCl are added, and the mixture is stirred for 10 minutes. Excess water is then added slowly until a precipitate forms. This is filtered off, washed with water and recrystallized from ethanol. 19 g (47% of theory) of colorless crystals, of melting point 236°–238° C., are obtained.

$C_{12}H_{11}NO_2$ (201): calculated: C 71.6; H 5.5; N 7.0. found: C 71.8; H 5.5; N 6.8.

EXAMPLE II

3-Ethyl-5-(2-hydroxy-styryl)-isoxazole

Using the method described in Example I, 6 g (0.02 mole) of diethyl (3-ethyl-isoxazol-5-yl)-methanephosphonate and 4.4 g (0.02 mole) of o-(1-methoxyethoxy)-benzaldehyde are reacted and the product is recrystallized from isopropanol. 1.7 g (32% of theory) of colorless crystals, of melting point 175°–176° C., are obtained.

$C_{13}H_{13}NO_2$ (215): calculated: C 72.5; H 6.1; N 6.5; found: C 72.5; H 6.2; N 6.6.

EXAMPLE III

3-Isopropyl-5-(2-hydroxy-styryl)-isoxazole

Using the method described in Example I, 32 g (0.12 mole) of diethyl (3-isopropyl-isoxazol-5-yl)methanephosphonate and 22 g (0.12 mole) of o-(1-methoxyethoxy)-benzaldehyde are reacted and the product is recrystallized from toluene. 20 g (73% of theory) of colorless crystals, of melting point 129°–133° C., are obtained.

$C_{16}H_{15}NO_2$ (229): calculated: C 73.3; H 6.6; N 6.1. found: C 73.7; H 6.7; N 5.8.

EXAMPLE IV 3-tert.-Butyl-5-(2-hydroxy-styryl)-isoxazole

Using the method described in Example I, 35 g (0.13 mole) of diethyl (3-tert.-butyl-isoxazol-5-yl)methanephosphonate and 23 g (0.13 mole) of o-(1-methoxyethoxy)-benzaldehyde are reacted and the product is recrystallized from toluene. 24.8 g (78% of theory) of colorless crystals, of melting point 152°–155° C., are obtained.

$C_{15}H_{17}NO_2$ (243) calculated: C 74.0; H 7.0; N 5.8. found: C 73.4; H 7.3; N 5.5.

EXAMPLE V

3-Methyl-5-[2-(2,3-epoxypropoxy)-styryl]-isoxazole 6.44 g of 55% strength sodium hydride in paraffin oil (0.15 mole) are introduced into 200 ml of absolute dimethylsulfoxide and 30 g (0.15 mole) of 3-methyl-5-(2-hydroxy-styryl)-isoxazole, dissolved in 50 ml of dimethylsulfoxide, are added dropwise, at room temperature. When the evolution of hydrogen has ceased, 20.2 g (0.15 mole) of epibromohydrin are added dropwise and the reaction mixture is stirred for 20 hours at room temperature. It is then poured onto 1.5 liters of ice water and the solid residue is filtered off and recrystallized from isopropanol. 26.2 g (68% of theory) of colorless crystals, of melting point 99°–100° C., are obtained.

$C_{15}H_{15}NO_3$ (257): calculated: C 70.0; H 5.9; N 5.4. found: C 70.0; H 5.9; N 5.5.

EXAMPLE VI

3-Ethyl-5-[2-(2,3-epoxypropoxy)-styryl]-isoxazole

This compound is prepared, using the method described in Example V, from 5.1 g of 55% strength sodium hydride (0.116 mole), 25.0 g (0.116 mole) of 3-ethyl-5-(2-hydroxystyryl)-isoxazole and 15.9 g (0.116 mole) of epibromohydrin. The reaction mixture is poured into sodium chloride solution and the batch is extracted by shaking with diethyl ether. The ether solution is dried with anhydrous sodium sulfate and evaporated down. 29.2 g (93% of theory) of a colorless oil are obtained.

EXAMPLE VII

3-Isopropyl-5-[2-(2,3-epoxypropoxy)-styryl]-isoxazole

This is prepared, using the method described in Example VI, from 3.4 g of 55% strength sodium hydride (0.078 mole), 18 g (0.078 mole) of 3-isopropyl-5-(2-hydroxystyryl)-isoxazole and 10.8 g (0.078 mole) of epibromohydrin. 21.5 g (97% of theory) of a colorless oil are obtained.

EXAMPLE VIII 3-tert.-Butyl-5-[2-(2,3-epoxypropoxy)-styryl]-isoxazole

This is prepared, using the method described in Example VI, from 3.8 g of 55% strength sodium hydride (0.086 mole), 21 g (0.086 mole) of 3-tert.-butyl-5-(2-hydroxystyryl)-isoxazole and 11.8 g (0.086 mole) of epibromohydrin. 25.0 g (97% of theory) of a colorless oil are obtained.

EXAMPLE IX 1.0 g of 3-methyl-5-[2-(2,3-epoxypropoxy)-styryl]-isoxazole is dissolved in 20 ml of a 3 N solution of hydrogen chloride in ether and the mixture is left to stand for 12 hours at room temperature. The resinous material formed is separated off and chromatographed over silica gel, using chloroform. The product eluates are evaporated to dryness under reduced pressure and the crude product is then recrystallized from an acetone/cyclohexane mixture. 3-Methyl-5-[2-(2-hydroxy-3-chloropropoxy)]-isoxazole, which is pure according to NMR spectroscopy and has a melting point of 67°–68° C., is obtained.

$^1$H-NMR spectrum (CDCl$_3$, with TMS as internal standard): $\tau = 2.30$–3.15 (m, 6H), 3.92 (s, 1H), 5.60–5.92 (m, 3H), 6.24 (d, J=3.5 Hz, 2H) and 6.77 (broad s, OH). Preparation of the compounds according to the invention.

The melting points in all the Examples relate to the trans-isomer of the compound.

EXAMPLE 1

6.0 g of 3-methyl-5-[2-(2,3-epoxypropoxy)-styryl]-isoxazole and 5.0 g of 2-(3-trifluoromethylphenyl)-1,1-dimethylethylamine in 100 ml of isopropanol are refluxed for 10 hours. The residue which is left after distilling off the solvent is chromatographed over a silica gel dry column (about 500 g of silica gel/50 cm of column length), using chloroform. The residue obtained on evaporating the product eluates is dissolved in ethanol/ether and a solution of hydrogen chloride in ether is added until the salt has been completely precipitated. The precipitate of 3-methyl-5-[2-[2-hydroxy-3-(2-(3-trifluoromethylphenyl)-1,1-dimethylethylamino)-propoxy]-styryl]-isoxazole hydrochloride is filtered off, washed with dry ether and dried. Yield: 8.3 g (70% of theory), of melting point 170°–171° C.

$C_{26}H_{29}N_2O_3F_3 \cdot HCl$ (510.99): calculated: C 61.11; H 5.92; N 5.48; Cl 6.94. found: C 60.8; H 5.9; N 5.7; Cl 7.6.

The compounds listed in the Table which follows are obtained in the same manner from 3-methyl-5-[2-(2,3-epoxypropoxy)-styryl]-isoxazole and the corresponding amines. All the compounds are characterized by elementary analyses and $^1$H-NMR spectra.

TABLE

| No. | R$^4$ | R | Free amine or salt form | M.p. (°C.) |
|---|---|---|---|---|
| 2 | —CH$_2$—CH$_3$ | —CH(CH$_3$)—CH$_2$—CH$_2$—C$_6$H$_4$—OH | free amine | 97–100 |
| 3 | —CH$_3$ | —CH(CH$_3$)—CH$_2$—CH$_2$—C$_6$H$_4$—OH | free amine | 110–112 |
| 4 | —CH$_3$ | —CH$_2$—CH$_2$—C$_6$H$_3$(OCH$_3$)(OCH$_3$) | free amine × 0.5 H$_2$O | 80–83 |
| 5 | —CH$_3$ | —CH(CH$_3$)—CH$_2$—CH$_2$—C$_6$H$_5$ | free amine | 90–91 |
| 6 | —CH$_3$ | —CH$_2$—CH$_2$—C$_6$H$_4$—OCH$_3$ | HCl | 180–182 |

TABLE-continued

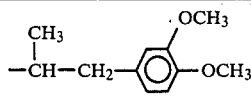

| No. | R⁴ | R | Free amine or salt form | M.p. (°C.) |
|---|---|---|---|---|
| 7 | —CH₃ | -CH(CH₃)-CH₂-[2,4-(OCH₃)₂-C₆H₃] | free amine | 121–125 |
| 8 | —CH₃ | -CH(CH₃)-CH₂-[4-OCH₃-C₆H₄] | ½ HOOC-CH=CH-COOH | 185–187 |
| 9 | —CH₃ | -CH(CH₃)-CH₂-[3-OCH₃-C₆H₄] | ½ HOOC-CH=CH-COOH | 154–156 |
| 10 | —CH₃ | -C(CH₃)₂-CH₂-[3-OCH₃-C₆H₄] | HCl | 128–130 |
| 11 | —CH₃ | -C(CH₃)₂-CH₂-[4-OCH₃-C₆H₄] | HCl | 145–146 |
| 12 | —CH₃ | -CH(CH₃)-CH₂-CH₂-[4-N(CH₃)₂-C₆H₄] | free amine × 0.5 H₂O | 103–105 |
| 13 | —CH₃ | -C(CH₃)₂-CH₂-CH₂-[4-OH-C₆H₄] | free amine | 139–140 |
| 14 | —CH₃ | -C(CH₃)₂-CH₂-C₆H₅ | HCl | 190 |
| 15 | —CH₃ | -CH(CH₃)-CH₂-CH₂-[3,4-methylenedioxy-C₆H₃] | HCl | 160–162 |
| 16 | —CH₃ | -C(CH₃)₂-CH₂-CH₂-[4-OCH₃-C₆H₄] | free amine × 0.5 H₂O | 83–85 |
| 17 | —CH₃ | -CH(CH₃)-CH₂-CH₂-[3,4-(OCH₃)₂-C₆H₃] | free amine | 100–102 |
| 18 | —CH₃ | -CH(CH₃)-CH₂-[3-CF₃-C₆H₄] | free amine | 82–84 |
| 19 | —CH₃ | -C(CH₃)₂-CH₂-[4-Cl-C₆H₄] | HCl · 0.5 H₂O | 179–181 |
| 20 | —CH₃ | -CH(CH₃)-CH₂-CH₂-[3,4,5-(OCH₃)₃-C₆H₂] | ½ HOOC-CH=CH-COOH | 190–192 |

TABLE-continued

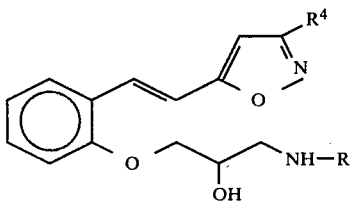

| No. | R⁴ | R | Free amine or salt form | M.p. (°C.) |
|---|---|---|---|---|
| 21 | —CH₃ | —CH(H)—CH₂—C₆H₄—OH | maleate (HOOC-CH=CH-COOH) | 162 |

Examples of formulations

1. Tablets:

| | | |
|---|---|---|
| (a) | An active compound of the formula I | 5 mg |
| | Lactose | 200 mg |
| | Methylcellulose | 15 mg |
| | Corn starch | 50 mg |
| | Talc | 11 mg |
| | Magnesium stearate | 4 mg |
| (b) | An active compound of the formula I | 20 mg |
| | Lactose | 178 mg |
| | Avicel | 80 mg |
| | Polywachs 6000 | 20 mg |
| | Magnesium stearate | 2 mg |
| | | 300 mg |
| (c) | An active compound of the formula I | 50 mg |
| | Polyvinylpyrrolidone(mean molecular weight 25,000) | 170 mg |
| | Polyethylene glycol(mean molecular weight 4,000) | 14 mg |
| | Hydroxypropylmethylcellulose | 40 mg |
| | Talc | 4 mg |
| | Magnesium stearate | 2 mg |
| | | 280 mg |

The active compound is moistened with a 10% strength aqueous solution of the polyvinylpyrrolidone, forced through a sieve of 1.0 mm mesh width and dried at 50° C. The granules obtained are mixed with polyethylene glycol (mean molecular weight 4,000), hydroxypropylmethylcellulose, talc and magnesium stearate and the mixture is molded to form tablets each weighing 280 mg.

2. Example of dragees

| | |
|---|---|
| An active compound of the formula I | 60 mg |
| Lactose | 90 mg |
| Corn starch | 60 mg |
| Polyvinylpyrrolidone | 6 mg |
| Magnesium stearate | 1 mg |
| | 217 mg |

The mixture of the active compound, lactose, corn starch and an 8% strength aqueous solution of the polyvinylpyrrolidone is granulated by forcing through a 1.5 mm sieve and the granules are dried at 50° C. and then forced through a 1.0 mm sieve. The granules from this operation are mixed with magnesium stearate and the mixture is molded to form dragee cores. The cores obtained are provided, in a conventional manner, with a coating which essentially consists of sugar and talc.

| 3. | Capsule formulation | |
|---|---|---|
| | An active compound of the formula I | 5.0 mg |
| | Magnesium stearate | 2.0 mg |
| | Lactose | 19.3 mg |
| 4. | Injection solution | |
| | An active compound of the formula I | 10 mg |
| | Sodium chloride | 9 mg |
| | Distilled water, q.s. to make up to 1.0 ml | |

We claim:

1. A compound of the general formula (I)

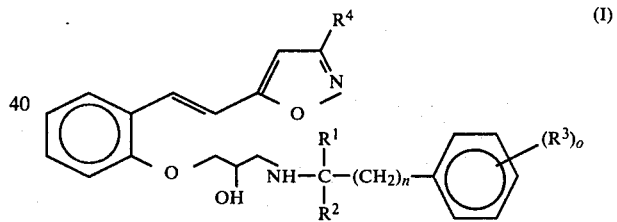

where n is 1 or 2, o is 1, 2 or 3, $R^1$ and $R^2$ are each hydrogen or straight-chain or branched alkyl of 1 to 5 carbon atoms, $R^3$ is hydrogen, hydroxyl, halogen, alkyl, alkoxy or alkylthio of 1 to 5 carbon atoms (the last-mentioned three groups each being unsubstituted, or mono-, di- or tri-substituted by halogen or mono- substituted by hydroxyl or alkoxy of 1 to 3 carbon atoms), alkenyl, alkynyl, alkynyloxy or cycloalkoxy, each of 2 to 6 carbon atoms in the alkyl and of 3 to 8 carbon atoms in the ring, or amino which is unsubstituted or is mono- or di-substituted by alkyl of 1 to 5 carbon atoms, and if o is 2 or 3, the $R^3$'s may be identical or different, or $R^3$ is methylene-dioxy or alkylene of 3 or 4 carbon atoms, and $R^4$ is alkyl of 1 to 4 carbon atoms, and its addition salts with acids.

2. 3-Methyl-5-[2-[2-hydroxy-3-(3-(4-hydroxyphenyl)-1-methylpropylamino)-propoxy]-styryl]-isoxazole.

3. 3-Methyl-5-[2-[2-hydroxy-3-(2-(3,4-dimethoxyphenyl)-1-ethylamino)-propoxy]-styryl]-isoxazole.

4. A therapeutic agent for treating hypertonia, angina pectoris or cardiac arrhythmias which comprises: an effective amount of a compound of the formula I

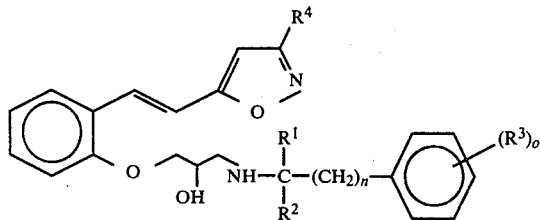

(I)

where n is 1 or 2, o is 1, 2 or 3, $R^1$ and $R^2$ are each hydrogen or straight-chain or branched alkyl of 1 to 5 carbon atoms, $R^3$ is hydrogen, hydroxyl, halogen, alkyl, alkoxy or alkylthio of 1 to 5 carbon atoms (the last-mentioned three groups each being unsubstituted, or mono-, di- or tri-substituted by halogen or mono-substituted by hydroxyl or alkoxy of 1 to 3 carbon atoms), alkenyl, alkynyl, alkynyloxy or cycloalkoxy, each of 2 to 6 carbon atoms in the alkyl and of 3 to 8 carbon atoms in the ring, or amino which is unsubstituted or is mono- or di-substituted by alkyl of 1 to 5 carbon atoms, and if o is 2 or 3, the $R^3$'s may be identical or different, or $R^3$ is methylene-dioxy or alkylene of 3 or 4 carbon atoms, and $R^4$ is alkyl of 1 to 4 carbon atoms, or a physiologically tolerated addition salt thereof with an acid, as the active compound, together with a pharmaceutically acceptable carrier or diluent.

* * * * *